United States Patent [19]
VanRheenen et al.

[11] Patent Number: 4,891,426
[45] Date of Patent: Jan. 2, 1990

[54] 16α-METHYL-17α 20-EPOXYSTEROID AND PROCESS

[75] Inventors: Verlan H. VanRheenen, Portage; Joel E. Huber, Texas township, Kalamazoo County, both of Mich.

[73] Assignee: The Upjohn Company, Kalamazoo, Mich.

[21] Appl. No.: 284,509

[22] Filed: Dec. 15, 1988

Related U.S. Application Data

[60] Division of Ser. No. 870,364, Jun. 6, 1986, abandoned, which is a continuation-in-part of Ser. No. 724,380, Apr. 18, 1985, Pat. No. 4,704,455, which is a continuation-in-part of Ser. No. 618,986, Jun. 11, 1984, abandoned.

[51] Int. Cl.$^4$ .................... C07J 71/00; A61F 31/58
[52] U.S. Cl. .......................... 540/4; 514/172
[58] Field of Search .............. 260/397.7, 4, 45, 5; 540/94, 4

[56]         References Cited
          U.S. PATENT DOCUMENTS

| 2,864,834 | 12/1958 | Mendelsohn et al. | 260/397.45 |
| 3,072,686 | 1/1963 | Wettstein et al. | 260/397.4 |
| 3,210,341 | 10/1965 | Lincoln et al. | 260/239.55 |
| 3,231,568 | 1/1966 | Julian et al. | 260/239.55 |
| 3,513,163 | 5/1970 | Brown | 260/239.55 |
| 3,700,660 | 10/1972 | Hempel et al. | 260/239.55 |
| 3,839,369 | 10/1974 | Hofmeister et al. | 260/397.45 |
| 3,876,633 | 4/1975 | Loken | 260/239.45 |
| 4,031,080 | 6/1977 | Palladino | 260/239.55 |
| 4,036,831 | 7/1977 | Loken et al. | 260/397.45 |
| 4,277,409 | 7/1981 | Warnant | 260/397.45 |
| 4,704,455 | 11/1987 | Van Rheenen et al. | 540/87 |

FOREIGN PATENT DOCUMENTS 2001990 of 0000 United Kingdom .

OTHER PUBLICATIONS

Organic Reactions in Steriod Chemistry, vol. II, J. Fried and J. A. Edwards, Van Nostrand Reinhold Co., NY (1972), pp. 75-76.
J. Am. Chem. Soc. 80, pp. 3160–3161 (1958).
J. Am. Chem. Soc. 80, p. 4428 (1958).
E. J. Corey in Tetrahedron Letters 26, p. 6019 (1985).
A. Alexakis in Tetrahedron Letters 27, p. 1047 (1986).

Primary Examiner—Nicholas S. Rizzo
Attorney, Agent, or Firm—Bruce Stein

[57]         ABSTRACT $C_{16}$-unsaturated corticoids are readily transformed to the corresponding 16α-methyl-17α-hydroxy corticoids by use of a Δ17(20)-20-silyl ether.

12 Claims, No Drawings

16α-METHYL-17α 20-EPOXYSTEROID AND PROCESS

The present patent application is a divisional of application Ser. No. 870,364 filed June 6, 1986, now abandoned, which is a continuation-in-part patent application of co-pending patent application Ser. No. 724,380, filed Apr. 18, 1985 now U.S. Pat. No. 4,704,455 which is a continuation-in-part application of patent application Ser. No. 618,986, filed June 11, 1984, now abandoned.

BACKGROUND OF THE INVENTION

Corticoids with a 16α-methyl group are known to be useful anti-inflammatory agents. These include dexamethasone (9α-fluoro-11β,17α-21-trihydroxy-16α-methylpregna-1,4-diene-3,20-dione), flumethasone 6α,-9α-difluoro-11β,17α,21-trihydroxy-16α-methylpregna-1,4-diene-3,20-dione) and paramethasone (6α-fluoro-11β,17α,21-trihydroxy-16α-methylpregna-1,4-diene-3,20-dione).

The 16-unsaturated corticoid (I) starting materials are known, see, U.S. Pat. Nos. 2,864,834, 3,210,341, 3,839,639, 4,031,080 and 4,277,409.

The transformation of 16-unsaturated pregnanes to 16α-methyl pregnanes by use of a Grignard reagent is known. The conjugate addition of a 16α-methyl group to a 16-unsaturated-20-keto steroid by means of a methyl Grignard reagent in the presence of a copper salt catalyst is well known, see Organic Reactions in Steroid Chemistry, Vol. II, J. Fried and J. A. Edwards, Van Nostrand Reinhold Co., NY, 1972, p 75. The product of such a reaction is the 16α-methyl -Δ17(20)-20-enolate, which according to Fried may be trapped as the 20-acetate, see p 76. While the addition can go 1,2 or 1,4 with a ratio of about 1:1, the addition of cuprous chloride gave exclusively 1,4-addition in yields of greater than 90%.

U.S. Pat. No. 3,231,568 (JULIAN) discloses the transformation of a 16-unsaturated progesterone to the corresponding 17α-hydroxy-16α-methylprogesterone. However, JULIAN's pregnane did not have a second α/β-unsaturated ketone in the form of a Δ4-3-ketone or Δ1,4-3-ketone as the steroid A-ring was 3,5-cyclo. In addition, JULIAN disclosed a progesterone having no $C_{21}$ functionality while the process of the present invention uses a 21-acylate which is sensitive to the Grignard reaction and is hydrolyzable. The C-ring of JULIAN contained no substitution and therefore was not sensitive to the oxidation reaction conditions. A further distinction is that JULIAN traps with acetate and the enol acetate of JULIAN is not reactive to the mild peracid conditions of the present process and hence would not form the desired 17,20-epoxide (III).

U.S. Pat. No. 4,031,080 (PALLADINO) uses copper for the conjugate addition reaction but produces an enol acetate which as JULIAN would teach would be unreactive to the mild and selective peracid reaction conditions of this invention producing the desired 17,20-epoxide (III). PALLADINO produces 17α-bromo-16α-methyl corticoid not a 17α-hydroxy-16α-methyl corticoid.

U.S. Pat. No. 4,277,409 (WARNANT) transforms a 16-unsaturated-21-acetate to a 16α-methyl-21-acetate, without introducing the necessary 17α-hydroxyl group while the process of the present invention introduces the desired 17α-hydroxyl group.

Great Britain Patent 2,001,990 discloses a process to transform a 16-unsaturated corticoid (I) to the corresponding 16α-methyl corticoid (V) by methylating the 16-unsaturated corticoid with copper catalyzed methyl grignard to produce the 16α-methyl-Δ17(20)-20-(magnesium bromide)enolate, followed by conversion by oxygenation to a 17α-hydroperoxide which is reduced to the corresponding 16α-methyl-17α,21-dihydroxy-20-one 21-acetate. The process of the present invention does not produce a 17α-hydroperoxide, but rather utilizes a 17α,20-epoxide (III) intermediate.

U.S. Pat. No. 3,072,686 (WETTSTEIN) discloses the transformation of a 16-unsaturated progesterone to a βα-hydroxy-16α-methylprogesterone by reacting the 16-unsaturated progesterone with a Grignard reagent and cuprous chloride. WETTSTEIN produces a Δ17(20)-20-enol acetate which is not reactive to the mild and selective peracid conditions of the present process and hence would not form the desired 17,20-epoxide (III).

Both J. Am. Chem. Soc. 80, 3160 (1958) and J. Am. Chem. Soc. 80, 4428 (1958) report the transformation of a 16-unsaturated progesterone to a 16α-methylprogesterone by use of a Grignard reagent followed by peracid oxidation to introduce the 17α-hydroxy group producing a 17α-hydroxy-16α-methylprogesterone. The 17α-hydroxy-16α-methylprogesterone is brominated and acylated to form the 21-acetoxy-17α-hydroxy-16α-methyl steroid.

E. J. Corey in Tetrahedron Letters 26, 6019 (1985), [COREY], discloses the reaction of a methylating agent (lithium dimethylcuperate) with an α,β-enone in the presence of a trapping agent (chlorotrimethylsilane). The significant difference between COREY and the present patent application is that COREY used preformed alkylcuperate where as the present invention generates the cuperate methylating agent in situ. Likewise, A. Alexakis in Tetrahedron Letters 27, 1047 (1986), [ALEXAKIS], discloses the reaction of lithium alkylcuperate with unsaturated esters in the presence of trimethylsilyl chloride and demonstrates an increased yield of the alkylated product. However, again ALEXAKIS like COREY used preformed cuperate whereas the present invention generates the cuperate methylating agent in situ.

U.S. Pat. No. 3,700,660 discloses a process of converting a 20-acyloxy-17,20-epoxy steroid to a 17α-acyloxy-20-keto steroid by use of a strong acid. U.S. Pat. No. 3,700,660 (HEMPEL) uses 20-acetate where the process of the present invention uses 20-silyl. The significance of this is that the Δ17(20)-20-enol silane (II) of the present invention is much more reactive than the corresponding 20-acylate of HEMPEL which permits epoxidation of the Δ17(20) double bond in steroids having other double bonds such as Δ4-3-keto, Δ1,4-3-keto, Δ9(11)-etc. whereas the 20-acylate of HEMPEL is limited to a non-functionalized steroid.

U.S. Pat. Nos. 3,513,163 and 4,036,831 disclose $C_{21}$ and $C_{11}$ trimethylsiloxy ethers respectively. Δ17(20)-20-O-substituted steroids are known where the substituent is an acyl group or a Grignard substituent (-Mg-X), see U.S. Pat. Nos. 3,072,686, 3,231,568 and 4,031,080. This Mg-X substituted compound while disclosed is not isolatable.

17α,20-Epoxy-16α-methyl-20-O-substituted steroids are disclosed in U.S. Pat. No. 3,876,633 where the 20-O-substituent is an acyl group, see claim 9.

Selective epoxidation of the Δ9(11) double bond over the Δ16 double bond in a Δ9(11),16-diene is set forth in U.S. Pat. No. 3,876,633. U.S. Pat. No. 3,876,633 discloses 9β11β-epoxy-Δ16-steroids where the A-ring is reduced. 9β,11β-epoxy-6α-fluoro-21-hydroxypregna-1,4,16-triene-3,20-dione 21-acetate is disclosed in U.S. Pat. No. 3,210,341, Example 9(b).

U.S. Pat. No. 4,036,831 discloses a process of protecting the 11β-hydroxyl group of a steroid, during subsequent reactions, with trimethylsilyl and the subsequent removal of the trimethylsilyl group by hydrolysis with 40–60% aqueous hydrogen fluoride.

SUMMARY OF THE INVENTION

Disclosed are the Δ17(20)-steroid (II A-C), a 17α,20-epoxide (III A-C) and the 17α-silyl ether (IV A-C).

Further disclosed is a process for the preparation of a Δ17(20)-steroid (II A-C) which comprises starting with a 16-unsaturated corticoid (I A-C) and (1) contacting the 16-unsaturated corticoid (I A-C) with a methylating agent in the presence of a copper catalyst and (2) contacting the product of step (1) with a silylating agent.

Also disclosed is a process for the preparation of a 17α,20-epoxide (III A-C) which comprises starting with a Δ17(20)-steroid (II A-C) and contacting it with a peracid.

Additionally disclosed is a process for the preparation of a Δ17(20)-steroid (II A-C) which comprises starting with a 16-unsaturated corticoid (I A-C) and contacting the 16-unsaturated corticoid (I A-C) with a methylating agent in the presence of a copper catalyst and a silylating agent.

DETAILED DESCRIPTION OF THE INVENTION

The 16-unsaturated corticoid (I A-C) starting materials are well known to those skilled in the art or can be readily prepared from known steroids by methods well known to those skilled in the art, see, for example, U.S. Pat. Nos. 2,773,080, 2,864,834, 3,210,341, 3,441,559, 3,461,144, 3,493,563, 3,839,369, 4,031,080, and 4,277,409.

The $C_3$ functionality of the Δ4-3-keto (A), Δ1,4-3-keto (B) and 3β-hydroxy-Δ5-(C) steroid does not have to be protected for the processes of the present invention. The 3β-hydroxy-Δ5-(C) steroid can have its $C_3$-hydroxyl group (Ca) protected as the silyl ether (Cb), ether (Cc) or ester (Cd), see Chart C. The free hydroxyl group (Ca) can be protected as the ether (Cc) or ester (Cd) as is well known to those skilled in the art. See Protective Groups in Organic Synthesis, Theodora W. Greene, Wiley & Sons, New York 1981. The ethers (Cc) are prepared by methods well known to those skilled in the art, see Steroid Reactions, Edited by Carl Djerassi, Holden-Day, San Francisco 1967, p 76–82. If the free 3β-hydroxyl group (Ca) is not protected as the ether (Cc) or ester (Cd) during the silation reaction, the free hydroxy group will be silated to form the silyl ether (Cb). During the silylation reaction, if the 3β-hydroxyl group is free and will be silylated, one additional equivalent of Grignard and silylating agent will be consumed. The $C_3$ protected forms of the 3β-hydroxy steroids (C) are considered equivalent to the non-protected or free form (C) respectively since the $C_3$ protecting groups are readily removable to convert the $C_3$ protected forms (Cb, Cc and Cd) to (A and C). The protecting group remains on until the hydrolysis (acid or base) of the 17α,20-epoxide. If acid hydrolysis is utilized and the $C_3$ protecting group is acid labile (Cb and Cc) it will be removed. Likewise if base hydrolysis is utilized and the $C_3$ protective group is base-sensitive (Cd) it will be removed. If the $C_3$ protecting group is not sensitive to the hydrolysis agent, the $C_3$ protected steroid will have to be treated with the appropriate agent to remove the $C_3$ protecting group.

It is preferred that the 16-unsaturated corticoid (I A-C) be a Δ4-3-keto (A) or a Δ1,4-3-keto (B) corticoid, more preferably a Δ1,4-3-keto (B) corticoid. It is preferred that the 16-unsaturated corticoid have the C-ring Δ9(11) or 9β,11β-epoxy. It is more preferred that the C-ring be 9β,11β-epoxy. It is preferred that $R_6$ be a hydrogen or fluorine atom, more preferred that $R_6$ be a hydrogen atom.

While it is preferred that the C-ring is Δ9(11) or 9β,11β-epoxy, the C-ring can be converted to the desired 9α-fluoro-11β-hydroxy functionality prior to the Grignard addition of the methyl group to the Δ16 double bond. If this is done, the 11β-hydroxy group should be protected as is well known to those skilled in the art, see for example, U.S. Pat. No. 4,036,831 where the protecting group is trimethylsilyl. Following the formation of the desired 16α-methyl corticoid, the (trimethylsilyl) protecting group is removed as is well known to those skilled in the art, see for example, U.S. Pat. No. 4,036,831.

The conjugate addition of a methylating agent, such as methyl Grignard, to a 16-unsaturated steroid to give the corresponding 16α-methyl steroid is well known, see Organic Reactions in Steroid Chemistry, Vol. II, J. Fried and J. A. Edwards, p 75 and U.S. Pat. No. 3,072,686.

The 16-unsaturated corticoid (I) is reacted with a methylating agent either followed by or in the presence of a trapping (silating) agent to give the enol silane Δ17(20)-steroid (II). It is preferred that the 16-unsaturated corticoid (I) is reacted with a methylating agent in the presence of the trapping agent rather than adding the trapping agent after the 16-unsaturated corticoid (I) is reacted with the methylating agent. The methylating agent is selected from the group consisting of $CH_3Cu$, $(CH_3)_2CuM$ or $CH_3MgQ$ and a catalytic amount of a copper (cupric) salt. The preferred methylating agent is methyl Grignard, preferably methyl magnesium chloride. The copper salt can be a cuprous salt such as cuprous chloride, bromide, iodide or cyanide or a cupric salt such as cupric chloride, cupric acetate, cupric propionate or complexes thereof. Examples of copper complexes include, cuprous bromide dimethylsulfide, cuprous chloride tris-n-butylphosphine and cuprous acetylacetonate. The nature of the copper complex is not critical. Hundreds (or thousands) of copper complexes are known which are considered equivalent to those set forth above. Preferred is cupric acetate or propionate, more preferred is cupric propionate. Additional catalysts which are considered equivalent to those disclosed above are well known to those skilled in the art, see, for example, Alfa Catalog, 1983–1984, Morton Thiokol, Inc., Alpha Products, PO Box 299, 152 Andover Street, Danvers, Mass. 01923. Depending on the physical facilities, it may be preferred that the cupric propionate be predissolved. Solvents suitable for the methylation reaction include those selected from the group consisting of THF, t-butylmethyl ether or dimethoxyethane. The reaction is performed in a range of from about −50° to about 20°, preferably at about −20°. When TLC indicates that no starting material is left (indicating the probable formation of an enolate intermediate), the silating agent is added and the resulting product is the Δ17(20) steroid (II). After the silylating agent is added the reaction temperature is kept in the range of about −25° to about 25°, preferably about 0°. It is preferable to filter the Grignard reaction mixture to prevent residual copper from entering the peracid reaction.

In the present invention the enolate intermediate is trapped with a trapping (silylating) agent which gives the Δ17(20)-20-(substituted silyl) product. Operable silylating agents include $(R_{20})_3$-Si-E, bistrimethylsilylacetamide. It is preferred that the silylating agent be of the formula $(R_{20})_3$-Si-E, more preferably trimethylsilyl chloride. Additional silylating agents considered equivalent to those disclosed above are well known to those skilled in the art, see, for example Silicon Compounds, Petrarch Systems. Inc., Bartram Rd. Bristol, PA 19007. While the silylating agent can be present while the enolate is formed or added after the enolate is formed, it is preferred that the silylating agent be present when the enolate is formed. The trapping of the enolate intermediate to produce the Δ17(20)-20-(acetate) is known, see U.S. Pat. No. 4,031,080 and Organic Reactions in Steroid Chemistry, Vol. II, supra, p. 76. These enol acylates are too unreactive to react selectively over A,B,C,-ring functionality such as Δ9(11). However, surprisingly and unexpectedly the Δ17(20)-20-(substituted silyl) derivative (II) is sufficiently reactive to react with electrophiles without affecting most of the other functionality in the A,B,C-rings.

The Δ17(20)-steroid (II) can be isolated if desired by means well known to those skilled in the art, see for example, Examples 1 and 8. However, since the desired product is the 16α-methyl corticoid (V), it is not necessary and preferable not to isolate the Δ17(20)-steroid (II) but rather to continue the reaction, see Examples 3-5, 11 and 12.

The Δ17(20)-steroid (II) is reacted with a peracid to produce the 17α,20-epoxide (III). While most peracids are operable, preferred peracids include m-chloroperbenzoic, perbenzoic, peracetic. The peracid-reaction conditions are well known to those skilled in the art. The peracid reaction does not significantly affect the Δ1, Δ4, or Δ9(11) functionalities in the remainder of the molecule, see Example 2. The solvent used during the methylation reaction producing the Δ17(20)-steroid (II) is removed and replaced by a non-polar solvent such as toluene, methylene chloride, ethyl acetate or t-butyl methyl ether. The inorganic salts remaining after the methylation reaction are removed by extraction. The peracid oxidation is performed in the temperature range of about −30° to 25°, preferably about −20°. When the reaction is complete, the excess peracid is destroyed by addition of an agent such as powdered sodium thiosulfate or sodium bisulfite. The 17α,20-epoxide (III) can be isolated if desired by means well known to those skilled in the art. However, since the desired product is the 16α-methyl corticoid (V), it is not necessary and preferable not to isolate the 17α,20-epoxide (III) but rather to continue the reaction in situ.

The 17α,20-epoxide (III) is transformed to the corresponding 16α-methyl corticoid (V) by acid or base hydrolysis. If base is used the 16α-methyl corticoid will be obtained as the 21-hydroxy compound ($R_{21}$ is a hydrogen atom). If acid is used the 16α-methyl corticoid will be the 21-ester ($R_{21}$ is $-CO-R_{21}'$). Suitable base hydrolyzing agents include hydroxide, carbonate, bicarbonate, alkoxide in alcohol at low temperature etc. It is preferred that the hydrolyzing agent be an acid. Suitable acids include mineral acids and other sufficiently strong acids such as p-TSA, sulfuric, hydrochloric, citric or acetic. The acid hydrolysis is sufficiently fast that the reaction is complete in about ½ hour at 20°-25°.

The 16α-methyl corticoids (V) are adrenocorticoid agents with glucocorticoid activity and are useful primarily for their anti-inflammatory effects as is well known to those skilled in the art. These include dexamethasone, flumethasone and paramethasone. One of the best known 16α-methyl corticoids is dexamethasone, see U.S. Pat. No. 3,375,261 and Reissue 28,369 as well as the Physicians Desk Reference 1983, 37th Edition, p 1270-1283.

If the C-ring of the 16α-methyl corticoid (V) is Δ9(11) or 9β,11β-epoxy, it is readily convertible to the pharmacologically active 9α-fluoro-11β-hydroxy C-ring by means well known to those skilled in the art.

DEFINITIONS

The definitions and explanations below are for the terms as used throughout the entire patent application including both the specification and the claims.

All temperatures are in degrees Centigrade.
TLC refers to thin-layer chromatography.
THF refers to tetrahydrofuran.
TMS refers to trimethylsilyl.
THP refers to tetrahydropyranyl.
EEE refers to (1-ethoxy) ethyl ether [—O—CH(CH$_3$)OCH$_2$CH$_3$].
p-TSA refers to p-toluenesulfonic acid monohydrate.
When solvent pairs are used, the ratio of solvents used are volume/volume (v/v).
DMSO refers to dimethylsulfoxide.
UV refers to ultraviolet spectroscopy.
NMR refers to nuclear (proton) magnetic resonance spectroscopy, chemical shifts are reported in ppm (δ) downfield from tetramethylsilane.
$[α]_D^{25}$ refers to the angle of rotation of plane polarized light (specific optical rotation) at 25° with the sodium D line (5893A).
Dexamethasone refers to 9α-fluoro-11β,17α,21-trihydroxy-16α-methylpregna-1,4-diene-3,20-dione.
Paramethasone refers to 6α-fluoro-11β,17α,21-trihydroxy-16α-methylpregna-1,4-diene-3,20-dione.
Flumethasone refers to 6α,9α-difluoro-11β,17α,21-trihydroxy-16α-methylpregna-1,4-diene-3,20-dione.
$R_3$ is alkyl of 1 thru 3 carbon atoms, a TMS, THP, or EEE group.
$R_3'$ is alkyl of 1 thru 5 carbon atoms or phenyl.
$R_6$ is a hydrogen or fluorine atom or methyl group.
$R_9$ is nothing, a hydrogen, fluorine or oxygen atom which makes the C-ring
  (a) Δ9(11) when $R_9$ is nothing and
  (b) 9β,11β-epoxide when $R_9$ and $R_{11}$ taken together are an oxygen atom.
$R_{11}$ is a hydrogen or oxygen atom, two hydrogen atoms, or α- or β-hydroxyl group or trimethylsilyl ether thereof which makes the C-ring
  (a) Δ9(11) when $R_{11}$ is a hydrogen atom,
  (b) 9β,11β-epoxide when $R_9$ and $R_{11}$ taken together are an oxygen atom and .... between $C_{11}$ and $R_{11}$ is a single bond, and
  (c) a ketone when $R_{11}$ is an oxygen atom and .... between $C_{11}$ and $R_{11}$ is a double bond.

$R_{20}$ is alkyl of 1 thru 4 carbon atoms or phenyl, the $R_{20}$'s can be the same or different.

$R_{21}$ is a hydrogen atom, —CO—$R_{21}'$ or —Si($R_{121}$)$_3$.

$R_{21}'$ is alkyl of 1 thru 4 carbon atoms or phenyl.

$R_{121}$ is alkyl of 1 thru 4 carbon atoms or phenyl, the $R_{121}$'s can be the same or different.

~ indicates that the attached group can be in either the α or β configuration.

.... is a single or double bond.

When the term "alkyl of _ through _ carbon atoms" is used, it means and includes isomers thereof where such exist.

X is a hydrogen atom or nothing; when X is nothing the .... at $C_3$ is a double bond and when X is a hydrogen atom the .... at $C_3$ is a single bond.

M is a lithium or magnesium ion.

Q is a chlorine, bromine or iodine atom.

E is a chlorine, bromine or iodine atom or —NRαRβ.

Rα is alkyl of 1 thru 5 carbon atoms or phenyl and may be connected or cyclized with Rβ in a ring with or without an oxygen or additional nitrogen atom.

Rβ is alkyl of 1 thru 5 carbon atoms or phenyl and may be connected or cyclized with Rα in a ring with or without an oxygen or additional nitrogen atom.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

20,21-Dihydroxy-16α-methylpregna-1,4,9(11),17(20)-tetraen-3-one 20-trimethyl silyl ether 21-acetate (IIB)

Methyl magnesium chloride in THF (2M, 4.5 ml) is added over a period of 2.5 hr to a mixture of 21-hydroxypregna-1,4,9(11),16-tetraene-3,20-dione 21-acetate (IB, U.S. Pat. No. 4,031,080, 2.0 g), THF (27 ml) and cupric acetate monohydrate (60 mg) previously cooled to −52°. The reaction temperature is kept at less than −40° during the Grignard addition. Following the Grignard addition, TLC indicated no starting material is left and the reaction mixture is quenched with trimethylsilyl chloride (1.1 ml). The reaction temperature is then slowly permitted to rise to 4° over a period of 3 hr at which time TLC indicated the reaction is complete. Toluene (15 ml) is added and the THF removed under reduced pressure maintaining the reaction medium at 10°–15°. The reaction mixture is first extracted with a pH 7 buffer, then 4 times with buffer (1 ml) and water (9 ml) and lastly with water. The layers are separated and the organic layer is dried over sodium sulfate at less than 0° for 48 hr. The toluene solution is divided into 35 two-ml portions, one of which is concentrated under reduced pressure to give the title compound.

EXAMPLE 2

17α,21-Dihydroxy-16α-methylpregna-1,4,9(11)-triene-3,20-dione 21-acetate (VB)

m-Chloroperbenzoic acid (0.556 g) is added dropwise to 20,21-dihydroxy-16α-methylpregna-1,4,9(11),17(20)-tetraen-3-one 20-trimethylsilyl ether 21-acetate (IIB, Example 1, one 35 ml aliquot) over about a 3 hr period keeping the bath temperature in the range of about −9° to about 0°. The reaction is quenched with sodium bisulfite (1M, 2.8 ml). Water is added and the phases are separated. The organic phase is washed with water, buffer and water, dried over sodium sulfate and concentrated to a solid. The solid is dissolved in ethyl acetate/hexane (5 ml) and crystals formed overnight. The filtrate is concentrated to a solid which is dissolved in methanol and cooled to 0°. The mixture is filtered, and the crystals washed with cold methanol.

TLC shows some 21-hydroxy compound (V) is present. Acetic anhydride (0.1 ml) and pyridine (0.4 ml) is added and the mixture stirred overnight. The mixture is worked up as is well known to those skilled in the art to give a solid which is crystallized from 40% aqueous methanol to give the title compound.

EXAMPLE 3

9β,11β-Epoxy-17α,21-dihydroxy-16α-methylpregna-1,4-diene-3,20-dione 21-acetate (VB)

A mixture of 9β,11β-epoxy-21-hydroxypregna-1,4,16-triene-3,20-dione 21-acetate (IB, Example 7, 3.824 g) and cupric acetate monohydrate (200 mg) and anhydrous THF (70 ml) at −15° is treated with methyl magnesium chloride (2.2M, 8.2 ml) added dropwise over 1 hour. After 10 minutes of stirring at −15° trimethylchlorosilane (1.64 ml) is added. The mixture is immediately warmed to 20°, stirred for 1 hour at which time TLC shows enol ether (II) formation to be complete. The mixture is added to toluene (100 ml) and this is washed with monobasic phosphate buffer (pH 4.25, 50 ml). The organic layer is separated and washed with water (2×50 ml) and each aqueous layer is back-extracted with toluene (15 ml). The organic phases are combined and concentrated at 55° under reduced pressure to a residue.

Toluene (30 ml) at 0° is added and the mixture treated with peroxyacetic acid (34.5%, 2.91 ml) containing sodium acetate (164 mg). The stirred mixture is warmed to 20° and after 10 minutes TLC indicates the peroxidation is complete. The excess peracid is destroyed by addition of powdered sodium thiosulfate (2.5 g) slurried in methanol (10 ml). Hydrochloric acid (6N, 3.0 ml) is added and the hydrolysis is complete in about 10 minutes. The mixture is added to toluene (75 ml) and the organic phase washed with water (2×50 ml), sodium carbonate solution (5%, 40 ml) and finally with water (50 ml). Each aqueous phase is back-extracted sequentially with toluene (20 ml). The organic phases are combined and concentrated under reduced pressure to a crystalline residue which is dissolved in hot ethyl acetate and filtered to remove traces of inorganics. Ethyl acetate (about 5 ml) is used for rinse. The combined volumes of the filtrate and rinse are reduced to about 10 ml. The solids formed and after about 1 hour hexane (4 ml) is added. After standing at 30°–40° for 2 hours the slurry is cooled to 20°, and the solids collected by vacuum filtration. The solids are washed with cold ethyl acetate:hexane, 1:1 (3 ml), and dried under reduced pressure at 50°–60° for 3 hours to give the title compound, mp 180°–186° with softening at about 135°; NMR (CDCl$_3$) 0.89, 0.92, 1.43, 3.18 and 4.83 δ.

EXAMPLE 4

9β,11β-Epoxy-6α-fluoro-17α,21-dihydroxy-16α-methylpregna-1,4-diene-3,20-dione (VB)

A mixture of 9β,11β-epoxy-6α-fluoro-21-hydroxy-1,4,16-triene-3,20-dione 21-acetate (IB, U.S. Pat. No. 3,210,341, 8.009 g) cupric acetate monohydrate (400 mg) and tri-n-butyl phosphine (1 ml) in anhydrous THF (120 ml) at −11° is treated with methyl magnesium chloride (1.95M, 26.5 ml) added dropwise over 1 hour. Trimethyl chlorosilane (4 ml) at −8° is then added. The mixture is immediately allowed to warm to 14° and after 20 minutes TLC indicates the reaction is complete. The mixture is added to ethyl acetate (300 ml) and washed with ammonium hydroxide:saturated ammonium chloride, 1:1 (2×75 ml). Each aqueous extract is sequentially washed with the same portion of ethyl acetate (210 ml). The combined organic phases are then concentrated at 45° under reduced pressure to an oil. The oil is taken up in methylene chloride (120 ml) at −10° and treated with m-chloroperoxybenzoic acid (85%, 6.092 g) and after 1.5 hours TLC indicates the epoxidation is complete. The mixture is vacuum distilled to replace the solvent with methanol (100 ml) and then the mixture is treated with saturated sodium carbonate (20 ml). After stirring 16 hours at 20°–25° and 5.25 hours at 55° TLC showed the hydrolysis is complete. After cooling to 20°–25° water (100 ml) is added and the pH adjusted to 7.5 using acetic acid (0.2 ml). Water (160 ml) is then added portion-wise at 5°. The solids that formed are collected by filtration, washed with 0° methanol in water (25:75, 50 ml) and dried under reduced pressure at about 84° over 16 hours to give the title compound, mp 241°–241.5°; $[\alpha]D^{25} = +45.7°$ (DMSO); UV $\lambda_{max}=245$ nm ($\epsilon=15,300$); NMR (CDCl$_3$/DMSO-d$_6$) 0.82, 0.82, 1.40, 3.30, 4.30 and 5.52 δ.

EXAMPLE 5

17α,21-Dihydroxy-16α-methylpregna-4,9(11)-diene-3,20-dione 21-acetate (VA)

Methyl magnesium chloride in THF (2M, 6.2 ml) is added to a mixture of 21-hydroxypregna-4,9(11),16-triene-3,20-dione 21-acetate (IA, U.S. Pat. No. 4,216,159, 3.68 g) and cupric acetate monohydrate (200 mg) in dry THF (100 ml) at −50° over a period of 17 minutes. The mixture is stirred at −45° to −50° for 20 minutes and then treated with trimethylchlorosilane (1.9 ml) and allowed to warm to 20°–25°. After 1.5 hours at 20°–25° TLC indicates the enol silyl ether formation is complete. The reaction mixture is added to ethyl acetate (150 ml) and this mixture is washed with cold sulfuric acid (5%, 200 ml), the layers are separated, the aqueous layer is back-extracted with ethyl acetate (25 ml). The original organic layer is washed with cold water (2×150 ml) which in turn was back-extracted with additional ethyl acetate. The organic layers phases are combined and concentrated under reduced pressure to about 100 ml.

m-Chloroperoxybenzoic acid (85%, 1.72 g) is added and the mixture stirred 1 hour at −15° following which another 300 mg of peracid is added and the mixture stirred at 20° overnight. The excess peracid is destroyed by treatment with sodium bisulfite solution (10%, 20 ml). The mixture is stirred for 20 minutes and then diluted with toluene (200 ml). The mixture is then washed with sulfuric acid (5%, 100 ml) and water (2×100 ml). After concentration to dryness under reduced pressure the residue is dissolved in methanol (100 ml) and treated with hydrochloric acid (3N, 0.5 ml). The mixture is again concentrated to a higher boiling residue which is taken up in toluene (200 ml). This mixture is washed with saturated sodium carbonate (100 ml) to remove the m-chlorobenzoic acid. Finally the organic layers are washed with water (2×100 ml) and concentrated as above. The residue dissolved in hot methanol (20 ml) for crystallization. After cooling to 0° for several hours a solid is obtained which is collected by vacuum filtration. The product is washed with cold methanol and dried at 20° to give the title compound; NMR 0.73, 0.93, 1.33 and 4.98 δ.

EXAMPLE 6

9β,11β-Epoxy-21-hydroxypregna-4,16-diene-3,20-dione 21-acetate (IA)

Following the general procedure of U.S. Pat. No. 3,876,633 and making non-critical variations, but starting with 21-hydroxypregna-4,9(11),16-triene-3,20-dione 21-acetate (U.S. Pat. No. 2,773,080), the title compound is obtained, mp 129°–130.5°.

EXAMPLE 7

9β,11β-Epoxy-21-hydroxypregna-1,4,16-triene-3,20-dione 21-acetate (IB)

Following the general procedure of U.S. Pat. No. 3,876,633 and making non-critical variations, but starting with 21-hydroxypregna-1,4,9(11),-16-tetraene-3,20-dione 21-acetate (U.S. Pat. No. 2,864,834) the title compound is obtained, mp 163.5°–165°.

EXAMPLE 8

9β,11β-Epoxy-17α,21-dihydroxy-16α-methylpregna-1,4-diene-3,20-dione (VB)

A mixture of 9β,11β-epoxy-21-hydroxypregna-1,4,16-triene-3,20-dione 21-acetate (IB, Example 7, 7.650 g) and cupric acetate monohydrate (400 mg) in dry THF (130 ml) is stirred under nitrogen. The temperature is adjusted to −20° and 1,1,3,3-tetramethylurea (5.0 ml) is added. Methyl magnesium chloride (2M, 16.6 ml) is added dropwise over 50 min at −17° to −19°. TLC indicates the Grignard reaction is complete. The mixture is stirred for 40 min at −19°, following which the magnesium enolate is quenched with trimethylchlorosilane (3.28 ml). The temperature rises to 25° during the 1 hr stir period. TLC shows this reaction is complete. The mixture is added to toluene (150 ml) and monobasic potassium phosphate buffer (pH 4.3, 10%, 50 ml). The aqueous layer is extracted with toluene (25 ml) and then is discarded. The two organic layers are washed sequentially with water (2×50 ml), then combined and concentrated to a high boiling residue.

The residue containing the Δ17(20)-20-enol silane is dissolved in toluene (60 ml). After cooling to −5°, 5.9 ml of 4.4M peroxyacetic acid containing sodium acetate (91 mg) is added and the mixture stirred for 80 min. TLC shows the epoxidation is complete. The excess peracid is destroyed with aqueous sodium bisulfite (1.5M, 10 ml) at about 0°.

After stirring 5 min the mixture is added to toluene (40 ml) and water (55 ml). The layers are separated and the aqueous phase is extracted with toluene (20 ml) and then discarded. The two organic layers are washed sequentially with saturated sodium bicarbonate (20 ml) and water (35 ml). The combined organic layers are filtered thru cotton and concentrated to a high boiling residue of the 17α,20-epoxide.

The epoxide is taken up in methanol (60 ml) and treated with p-TSA (5 mg) at 21°. After 6 min TLC indicates the epoxide is opened and the 16α-methyl corticoid has formed (as the 21-acetate). A saturated sodium carbonate solution (1.9 ml) is added and the slurry stirred at 55° for 45 min. TLC indicates the hydrolysis is complete. Water (30 ml) is added and the slurry is stored at 0° overnight. The solids are collected by filtration, washed with methanol/water (1/1) and dried under reduced pressure at 70° for 4.5 hr to give the title compound, mp 238°–239.5°.

EXAMPLE 9

9β,11β-Epoxy-20,21-dihydroxy-16α-methylpregna-1,4,17-(20)-trien-3-one-20-trimethylsilyl ether 21-acetate (IIB)

Following the general procedure of Example 1 and making non-critical variations but starting with 9β,11β-epoxy-21-hydroxy-1,4,16-triene-3,20-dione 21-acetate (IB, Example 7) the title compound is obtained.

EXAMPLE 10

9α-Fluoro-11β,21-dihydroxypregna-1,4,16-triene-3,20-dione 21-acetate (IB)

9β,11β-Epoxy-21-hydroxypregna-1,4,16-triene-3,20-dione 21-acetate (IB, Example 7, 15.3 g) is added to a stirred mixture of aqueous hydrogen fluoride (72%, 55 ml) and methylene chloride (15 ml) at −25° in a 200 ml monel reactor fitted with a mechanical agitator. About 30 ml of methylene chloride is used as a rinse. The mixture is stirred at −22° for 2.5 hr and then at −4° to −11° for 4.0 hr. The mixture is treated with THF (35 ml) at −10° and then quenched carefully by slow addition of a mixture of THF (60 ml), aqueous potassium carbonate (47%, 202 ml) and water (100 ml). After stirring 20 min the mixture is added to toluene (400 ml) and water (400 ml). The phases are separated and the organic layer is washed with water (3×150 ml), dried by filtration thru cotton and concentrated to about 150 ml. Methylene chloride (about 150 ml) and magnesol (0.90 g) is added to the mixture. After 15 min the magnesol is removed by filtration. The filtrate is again concentrated to 150 ml and then cooled to 0°. Solids form after stirring at 0° for 3 hr and the product is collected by filtration. The solids are washed with toluene (2×25 ml) and dried at 60° for 3 hr under vacuum to give the title compound, mp=223°–225°; NMR (CDCl$_3$) 1.27, 1.59, 4.29, 4.93 and 6.77 δ.

EXAMPLE 11

9α-Fluoro-11β,20,21-trihydroxy-16α-methylpregna-1,4,17-(20)-trien-3-one 11,20-bis(trimethylsilyl)ether 21-acetate (IIB)

A solution of copper (II) propionate (151 mg) in dry THF (60 ml) is cooled to −30° and then treated with methyl magnesium chloride (2M, about 1 ml) in order to reduce the copper to copper (I). 9α-Fluoro-11β,21-dihydroxypregna-1,4,16-triene-3,20-dione 21-acetate (IB, Example 10, 2.025 g) is added to the copper mixture. The temperature is adjusted to −33° and the above Grignard reagent (3.0 ml) is added. A slurry forms which is dissolved when treated with trimethylsilyl chloride (1.50 ml). After stirring 1 hr at −40° another 7.4 ml of the Grignard reagent is added portionwise over 50 min. The mixture is stirred another 2 hr and the temperature is allowed to rise to −26°. Then trimethylsilyl chloride (2.0 ml) is added over 1.25 hr at −15°. TLC indicates formation of the Δ17(20)-enol ether is not complete after another 0.5 hr at −15°. Grignard reagent (3.0 ml) is added at −35°. After 20 min the mixture is added to toluene (150 ml). This mixture is washed with 150 ml of water containing 20 ml of 5% phosphate buffer (pH 6.5). The phases are separated and the organic layer is washed with water (2×75 ml) and then dried by filtration thru cotton to give the title compound in solution.

EXAMPLE 12

17α,20-Epoxy-9α-fluoro-11β,20,2-trihydroxy-16α-methylpregna-1,4-dien-3-one 11,20-bis(trimethylsilyl)ether 21-acetate (IIIB)

The above filtrate (Example 11) is concentrated to about 50 ml and after cooling this mixture to −17°, peroxyacetic acid (4.44M, 3.37 ml) containing sodium acetate (67 mg) is added. The mixture is stirred for 4 hr while the temperature is allowed to rise to 7°. The mixture is diluted with toluene and then washed with water (75 ml), dilute sodium sulfite and finally with water (75 ml). Each aqueous wash is back-extracted with toluene (50 ml). The organic phases are combined, and concentrated under vacuum distillation to give a higher boiling residue of crude 17(20)-epoxide-20-trimethylsilyl ether (III).

EXAMPLE 13

9α-Fluoro-11β,17α,21-trihydroxy-16α-methylpregna-1,4-diene-3,20-dione 21-acetate (VB)

The residue (Example 12) is dissolved in methanol (30 ml) and allowed to stand at room temperature. After 0.75 hr the mixture is concentrated to 15 ml and water (10 ml) is added. The mixture is filtered to remove traces of insoluble material. The filtrate is diluted with more water and a waxy solid is collected by decantation. The solid is dried and then recrystallized from acetone/hexane (½, 35 ml). The solids are collected by filtration, washed with acetone/hexane (½, 5 ml) and dried at room temperature to give the title compound. A pure sample of the title compound is obtained by column chromatography followed by crystallization from acetone/hexane (1/1), mp=227°–229°; NMR (CDCl$_3$) 0.89, 1.03, 1.57, 4.29 and 4.93 δ.

EXAMPLE 14

17α,20-Epoxy-20,21-dihydroxy-16α-methylpregna-1,4,9(11)-trien-3-one 20-trimethylsilyl ether 21-acetate (IIIB)

Following the general procedure of Example 12 and making non-critical variations, but starting with 20,21-dihydroxy-16α-methylpregna-1,4,9(11),17(20)-tetraen-3-one 20-trimethylsilyl ether 21-acetate (IIB, Example 1) the title compound is obtained.

EXAMPLE 15

9β,11β,17α,20-Diepoxy-20,21-dihydroxy-16α-methylpregna-1,4-dien-3-one 20-trimethylsilyl ether 21-acetate (IIIB)

Following the general procedure of Example 12 and making non-critical variations, but starting with 9β,11β-epoxy-20,21-dihydroxy-16α-methylpregna-1,4,17(20)-trien-3-one 20-trimethylsilyl ether 21-acetate (IIB, Example 9) the title compound is obtained.

EXAMPLE 16

9β,11β-Epoxy-17α,21-dihydroxy-16α-methylpregna-1,4-diene-3,20-dione 21-acetate (VB)

A mixture of copper (II) propionate (802 mg) in THF (90 ml) and tetramethylurea (5 ml) are cooled to −25° under nitrogen and treated with about 3 ml of methyl magnesium chloride (2M) in order to convert the blue copper (II) to the yellow-green copper (I) species. Then methylene chloride (90 ml), trimethylsilyl chloride (6.56 ml) and 9β,11β-epoxy-21-hydroxypregna-1,4,16-triene-3,20-dione 21-acetate (IB, Example 7, 15.30 g) are added and the temperature is lowered to −33°. A total of 28 ml of the above Grignard reagent is added to the slurry over a 2.0 hr period. The temperature is maintained at in the range of −33° to −38° during this time. When TLC indicates the reaction to the Δ17(22)-corticoid silyl ether (II) is complete, the mixture is treated at −10° with ammonium chloride (0.5M, 200 ml). The layers are separated and the organic layer is washed with water (200 ml). The separate aqueous layers are extracted with methylene chloride (2×50 ml). The organic extracts are combined and concentrated to give the corresponding Δ17(22)-corticoid silyl ether.

This material is dissolved in toluene (100 ml). Sodium acetate (1.0 g) followed by peroxyacetic acid (34%, 11.8 ml) are added at −16°. The mixture is stirred at −16° to 10° over 19 hr following which the excess peracid si quenched with sodium bisulfite (1M). Water (100 ml) is added and the layers are separated. The aqueous layer is extracted with toluene (75 ml). The organic layers are washed sequentially with water (2×75 ml) and then combined, filtered thru cotton and concentrated. The concentrate is dissolved in methanol and reconcentrated to remove all the toluene and give the corresponding 17α,20-epoxide.

The 17α,20-epoxide is dissolved in methylene chloride (40 ml) and methanol (70 ml) under nitrogen. The temperature is adjusted to 40° and a solution of potassium bicarbonate (200 mg) and potassium carbonate (200 mg) in water (5 ml) is added. This mixture is stirred at reflux (about 42°). After 75 min, TLC indicates both the $C_{20}$ trimethylsilyl and $C_{21}$ acetate groups have been removed. The reaction is stopped by addition of acetic acid (0.6 ml) and the mixture concentrated at ordinary pressure to about 50 ml. The resulting slurry is cooled to about 0° and the solids are collected, washed with cold methanol and dried under reduced pressure at 60° to give the title compound, mp 260° with dec.

CHART A

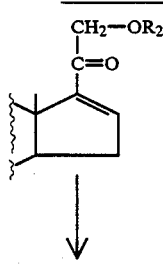

(I)

CHART A

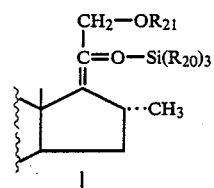

(II)

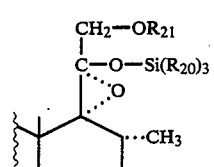

(III)

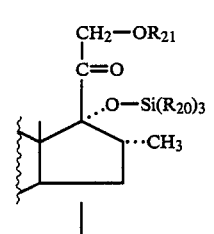

(IV)

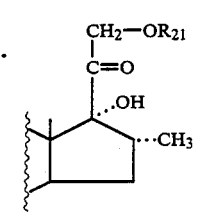

(V)

CHART B

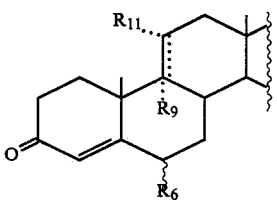

(A)

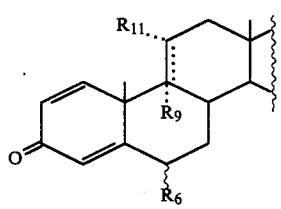

(B)

-continued
CHART B

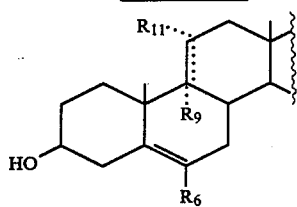

CHART C

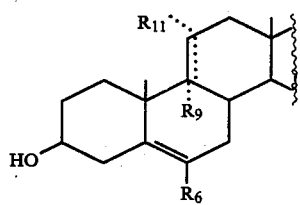

(Ca)

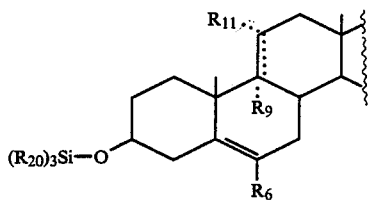

(Cb)

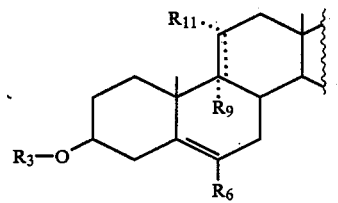

(Cc)

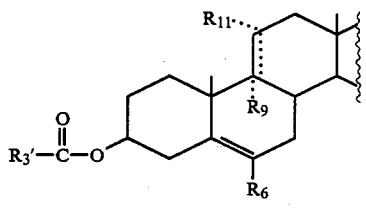

(Cd)

ENUMERATED EMBODIMENTS

1. A 17α-silyl ether of the formula

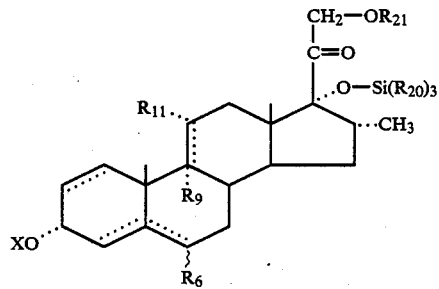

(IV A-C)

and the C$_3$-protected forms of the 3β-hydroxy-Δ5-(C) A-ring where

R$_6$ is a hydrogen or fluorine atom or methyl group;

R$_9$ is nothing, a hydrogen, fluorine or oxygen atom (C) which makes the C-ring (a) Δ9(11) when R$_9$ is nothing and (b) 9β,11β-epoxide when R$_9$ and R$_{11}$ taken together are an oxygen atom;

R$_{11}$ is a hydrogen or oxygen atom, two hydrogen atoms, or α- or β-hydroxyl group or trimethylsilyl ether thereof which makes the C-ring (a) Δ9(11) when R$_{11}$ is a hydrogen atom, (b) 9β,11β-epoxide when R$_9$ and R$_{11}$ taken together are an oxygen atom and .... between C$_{11}$ and R$_{11}$ is a single bond, and (c) a ketone when R$_{11}$ is an oxygen atom and .... between C$_{11}$ and R$_{11}$ is a double bond;

R$_{20}$ is alkyl of 1 thru 4 carbon atoms or phenyl, the R$_{20}$'s can be the same or different;

R$_{21}$ is a hydrogen atom, —CO—R$_{21}'$ or —Si(R$_{121}$)$_3$;

R$_{21}'$ is alkyl of 1 thru 4 carbon atoms or phenyl;

R$_{121}$ is alkyl of 1 thru 4 carbon atoms or phenyl, the R$_{121}$'s can be the same or different;

~ indicates that the attached group can be in either the α or β configuration;

.... is a single or double bond; and

X is a hydrogen atom or nothing; when X is nothing the .... at C$_3$ is a double bond and when X is a hydrogen atom the .... at C$_3$ is a single bond.

2. A 17α-silyl ether according to Enumerated Embodiment 1 where the 17α-silyl ether (IV A-C) is a Δ4-3-keto (A) or Δ1,4-3-keto (B) steroid.

3. A 17α-silyl ether according to Enumerated Embodiment 1 where the 17α-silyl ether (IV A-C) is a 3β-hydroxy-Δ5 (C) steroid in the free form

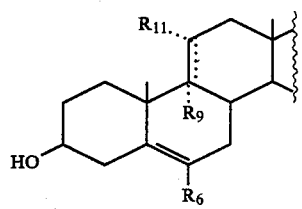 (Ca)

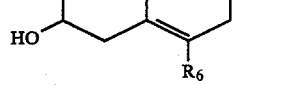

or C$_3$ protected form selected from the group consisting of

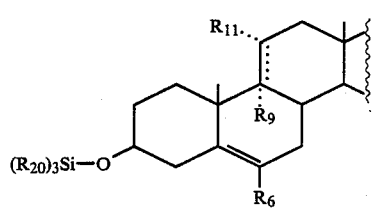 (Cb)

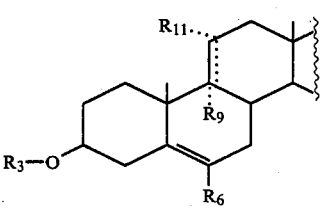 (Cc)

and

-continued

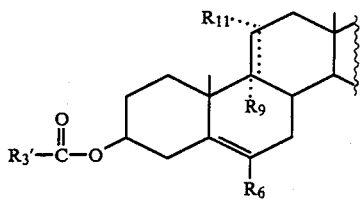

where
R$_3$ is alkyl of 1 thru 3 carbon atoms, a TMS, THP or EEE group;
R$_3'$ is alkyl of 1 thru 5 carbon atoms or phenyl;
TMS refers to trimethylsilyl;
THP refers to tetrahydropyranyl;
EEE refers to (1-ethoxy) ethyl ether [—O—CH(CH$_3$)OCH$_2$CH$_3$];
where R$_6$, R$_9$, R$_1{}^1$, R$_{20}$ and ~ are defined in Enumerated Embodiment 1.

4. A 17α-silyl ether according to Enumerated Embodiment 1 where R$_6$ is a hydrogen atom.

5. A 17α-silyl ether according to Enumerated Embodiment 1 where R$_9$ is nothing or an oxygen atom and where R$_{11}$ is a hydrogen atom or an oxygen atom making the C-ring Δ9(11) or a 9β,11β-epoxide.

6. A 17α-silyl ether according to Enumerated Embodiment 1 where R$_{20}$ is selected from the group consisting of methyl, isopropyl, t-butyl or phenyl.

7. A 17α-silyl ether according to Enumerated Embodiment 1 where R$_{20}$ is methyl or phenyl.

8. A 17α-silyl ether according to Enumerated Embodiment 1 where R$_{21}$ is —CO—R$_{21}'$ and R$_{21}'$ is selected from the group consisting of methyl, ethyl or phenyl.

9. 9β,11β-Epoxy-21-hydroxypregna-4,16-diene-3,20-dione 21-acetate.

10. 9β,11β-Epoxy-21-hydroxypregna-1,4,16-triene-3,20-dione 21-acetate.

We claim:
1. A 17α,20-epoxy steroid of the formula

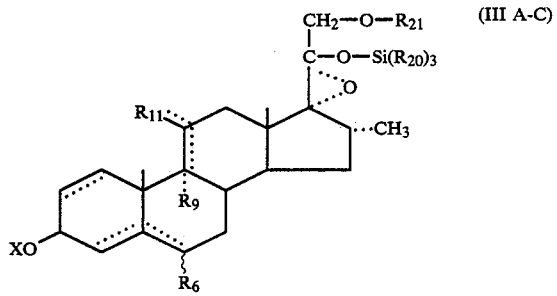

and the C$_3$-protected forms of the 3β-hydroxy-Δ5-(C) A-ring where
R$_6$ is a hydrogen or fluorine atom or methyl group;
R$_9$ is nothing, a hydrogen, fluorine or oxygen atom which makes the C-ring
 (a) Δ9(11) when R$_9$ is nothing and
 (b) 9β,11β-epoxide when R$_9$ and R$_{11}$ taken together are an oxygen atom;
R$_{11}$ is a hydrogen or oxygen atom, two hydrogen atoms, or α- or β-hydroxyl group or trimethylsilyl ether thereof which makes the C-ring
 (a) Δ9(11) when R$_{11}$ is a hydrogen atom,
 (b) 9β,11β-epoxide when R$_9$ and R$_{11}$ taken together are an oxygen atom and ~ between C$_{11}$ and R$_{11}$ is a single bond, and
 (c) a ketone when R$_{11}$ is an oxygen atom and ~ between C$_{11}$ and R$_{11}$ is a double bond;
R$_{20}$ is alkyl of 1 thru 4 carbon atoms or phenyl, the R$_{20}$'s can be the same or different;
R$_{21}$ is a hydrogen atom, —CO—R$_{21}'$ or —Si(R$_{121}$)$_3$;
R$_{21}'$ is alkyl of 1 thru 4 carbon atoms or phenyl;
R$_{121}$ is alkyl of 1 thru 4 carbon atoms or phenyl, the R$_{121}$'s can be the same or different;
~ indicates that the attached group can be in either the α or β configuration;
 is a single or double bond; and
X is a hydrogen atom or nothing; when X is nothing the ~ at C$_3$ is a double bond and when X is a hydrogen atom the ~ at C$_3$ is a single bond.

2. A 17α,20-epoxy steroid according to claim 1 where the 17α,20-epoxy steroid (III A-C) is a Δ4-3-keto (A) or Δ1,4-3-keto (B) steroid.

3. A 17α,20-epoxy steroid according to claim 1 where the 17α,20-epoxy steroid (III A-C) is a 3β-hydroxy Δ5 (C)-steroid in the free form

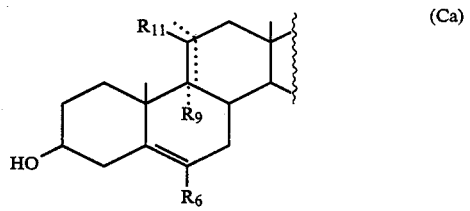

or C$_3$ protected form selected from the group consisting of

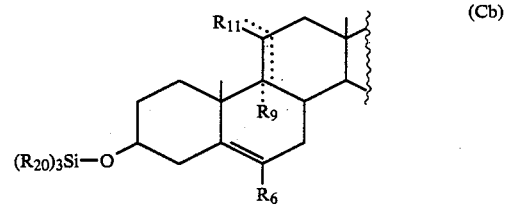

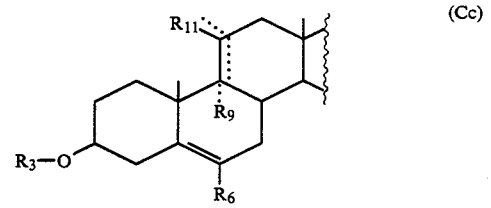

and

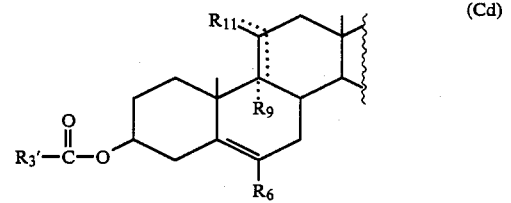

where
R$_3$ is alkyl of 1 thru 3 carbon atoms, a TMS, THP or EEE group;

$R_3'$ is alkyl of 1 thru 5 carbon atoms or phenyl;
TMS refers to trimethylsilyl;
THP refers to tetrahydropyranyl;
EEE refers to (1-ethoxy) ethyl ether [—O—CH(CH$_3$)OCH$_2$CH$_3$];
where $R_6$, $R_9$, $R_1^1$, $R_{20}$ and ⋯ are defined in claim 1.

4. A 17α,20-epoxy steroid according to claim 1 where $R_6$ is a hydrogen atom.

5. A 17α,20-epoxy steroid according to claim 1 where $R_9$ is nothing or an oxygen atom and where $R_{11}$ is a hydrogen atom or an oxygen atom making the C-ring Δ9(11) or a 9β,11β-epoxide.

6. A 17α,20-epoxy steroid according to claim 1 where $R_{20}$ is selected from the group consisting of methyl, isopropyl, t-butyl or phenyl.

7. A 17α,20-epoxy steroid according to claim 1 where $R_{20}$ is methyl or phenyl.

8. A 17α,20-epoxy steroid according to claim 1 where $R_{21}$ is —CO—$R_{21}'$ and $R_{21}'$ is selected from the group consisting of methyl, ethyl or phenyl.

9. A 17α,20-epoxy steroid according to claim 1 which is 17α,20-epoxy-20,21-dihydroxy-16α-methylpregna-1,4,9(11)-trien3-one 20-trimethylsilyl ether 21-acetate; 9β,11β;17α,20-diepoxy-20,21-dihydroxy-16α-methylpregna-1,4-dien-3-one 20-trimethylsilyl ether 21-acetate and 17α,20-epoxy-9α-fluoro-11β,20,21-trihydroxy-16α-methylpregna-1,4-dien-3-one 11,20-bis(trimethylsilyl)ether 21-acetate.

10. A process for the preparation of a 17α,20-epoxide of the formula

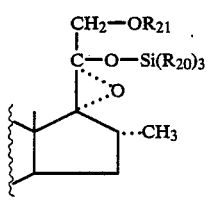

which comprises contacting a Δ17(20)-steroid of the formula

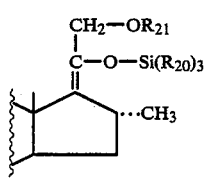

with a peracid where
$R_{20}$ is alkyl of 1 thru 4 carbon atoms or phenyl, the $R_{20}$'s can be the same or different,
$R_{21}$ is a hydrogen atom, —CO—$R_{21}'$ or —Si($R_{121}$)$_3$,
$R_{21}'$ is alkyl of 1 thru 4 carbon atoms or phenyl,
$R_{121}$ is alkyl of 1 thru 4 carbon atoms or phenyl, the $R_{121}$'s can be the same or different.

11. A process according to claim 10 where the Δ17(20) steroid (II) is selected from the group consisting of
Δ4-3-keto steroids

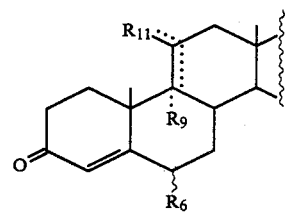

Δ1,4-3-keto steroids

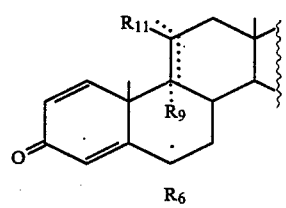

and 3β-hydroxy-Δ5 steroids

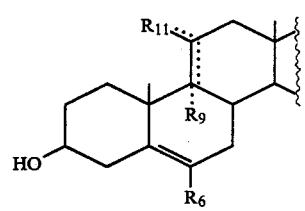

and the C$_3$ protected forms of the 3β-hydroxy-Δ5 (C) steroid

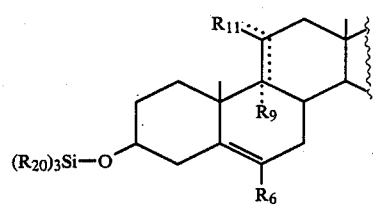

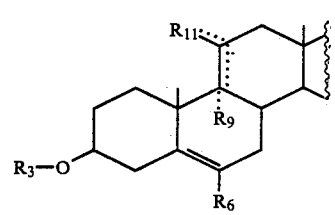

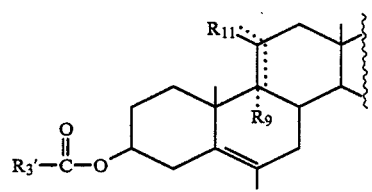

where
$R_3$ is alkyl of 1 thru 3 carbon atoms, a TMS, THP, or EEE group,
$R_3'$ is alkyl of 1 thru 5 carbon atoms or phenyl,
$R_6$ is a hydrogen or fluorine atom or methyl group, $R_9$ is nothing, a hydrogen, fluorine or oxygen atom which makes the C-ring
  (a) Δ9(11) when $R_9$ is nothing and
  (b) 9β,11β-epoxide when $R_9$ and $R_{11}$ taken together are an oxygen atom,
$R_{11}$ is a hydrogen or oxygen atom, two hydrogen atoms, or α- or β-hydroxyl group or trimethylsilyl ether thereof which makes the C-ring
  (a) Δ9(11) when $R_{11}$ is a hydrogen atom,
  (b) 9β,11β-epoxide when $R_9$ and $R_{11}$ taken together are an oxygen atom and .... between $C_{11}$ and $R_{11}$ is a single bond, and
  (c) a ketone when $R_{11}$ is an oxygen atom and .... between $C_{11}$ and $R_{11}$ is a double bond,
$R_{20}$ is alkyl of 1 thru 4 carbon atoms or phenyl, the $R_{20}$'s can be the same or different,
$R_{21}$ is a hydrogen atom, —CO—$R_{21}'$ or —Si($R_{121}$)$_3$,
$R_{21}'$ is alkyl of 1 thru 4 carbon atoms or phenyl,
$R_{121}$ is alkyl of 1 thru 4 carbon atoms or phenyl, the $R_{121}$'s can be the same or different,
~ indicates that the attached group can be in either the α or β configuration,
.... is a single or double bond,
TMS refers to trimethylsilyl;
THP refers to tetrahydropyranyl;
EEE refers to (1-ethoxy) ethyl ether [—O—CH(CH$_3$)OCH$_2$CH$_3$].

12. A process according to claim 10 where the peracid is selected from the group consisting of peracetic, perbenzoic, m-chloroperbenzoic.

* * * * *